United States Patent [19]
Greenberger et al.

[11] Patent Number: 5,993,801
[45] Date of Patent: *Nov. 30, 1999

[54] GENE THERAPY USING STROMAL CELLS

[75] Inventors: Joel S. Greenberger, Lincoln; Peter H. Levine, Worcester, both of Mass.

[73] Assignee: ALG Company, Marlboro, Mass.

[*] Notice: This patent is subject to a terminal disclaimer.

[21] Appl. No.: 08/914,631

[22] Filed: Aug. 19, 1997

Related U.S. Application Data

[63] Continuation of application No. 08/408,536, Mar. 22, 1995, Pat. No. 5,849,287, which is a continuation of application No. 08/166,595, Dec. 13, 1993, abandoned, which is a continuation of application No. 08/001,461, Jan. 7, 1993, abandoned, which is a continuation of application No. 07/879,779, May 6, 1992, abandoned, which is a continuation of application No. 07/748,088, Aug. 21, 1991, abandoned, which is a continuation of application No. 07/305,856, Feb. 2, 1989, abandoned.

[51] Int. Cl.$^6$ .................................................. A01N 63/00
[52] U.S. Cl. .................... 424/93.21; 424/93.1; 424/93.2; 514/44
[58] Field of Search ............................. 514/44; 424/93.1, 424/93.2, 93.21

[56] References Cited

U.S. PATENT DOCUMENTS

| | | | |
|---|---|---|---|
| 4,117,881 | 10/1978 | Williams et al. | 165/2 |
| 4,861,719 | 8/1989 | Miller | 435/236 |
| 5,399,493 | 3/1995 | Emerson et al. | 435/172.3 |
| 5,591,625 | 1/1997 | Gerson et al. | 435/240.2 |
| 5,849,287 | 12/1998 | Greenberger et al. | 424/93.21 |

FOREIGN PATENT DOCUMENTS

WO 91/18620  12/1991  WIPO .

OTHER PUBLICATIONS

Anderson, *Science*, 226:401–409 (1984).
Anklesaria et al., *PNAS*, 84:7681 (1987).
Boswell et al., *Exp. Hematol.*, 11:315–323 (1983).
Brunner et al., *Blood*, 81:631–638 (1993).
Gilabert et al., *Eur. J. Haematol.*, 53:93–99 (1994).
Kimura et al., *Br. J. Hematol.*, 69:9–12 (1988).
Nicol et al., *Blood*, 86 (Supp. 1):120a, Abstract No. 469 (1995).
Sorger et al., *In Vitro Cell. Dev. Biol. –Animal*, 31:671–683 (1995).
Toole et al., *Nature*, 312:342 (1984).

*Primary Examiner*—Brian R. Stanton
*Assistant Examiner*—Deborah J. R. Clark
*Attorney, Agent, or Firm*—Fish & Richardson P.C.

[57] ABSTRACT

A method of causing production and secretion into the bloodstream of a human patient of a biologically active enzyme for which the human patient suffers a deficiency; the method involves introducing into the human patient donor bone marrow stromal cells which have been transfected with a gene encoding the enzyme, so that the introduced cells can adhere to a bone cavity surface of the patient and produce and secrete the active enzyme.

20 Claims, 2 Drawing Sheets

GENE THERAPY USING STROMAL CELLS

This application is a continuation of copending application Ser. No. 08/408,536, filed Mar. 22, 1995, U.S. Pat. No. 5,849,287 Dec. 15, 1998, which is a continuation of application Ser. No. 08/166,595 filed on Dec. 13, 1993, now abandoned, which is a continuation application of Ser. No. 08/001,461, filed Jan. 7, 1993, now abandoned, which is a continuation application of Ser. No. 07/879,779, filed May 6, 1992, now abandoned, which is a continuation application of Ser. No. 07/748,088, filed Aug. 21, 1991, now abandoned, which is a continuation of application of Ser. No. 07/305,856, filed Feb. 2, 1989, now abandoned.

This invention was made with Government support under grants P01HD19767 and R01CA39851 from the National Institutes of Health. The Government therefore may have certain rights in the invention.

BACKGROUND OF THE INVENTION

This invention relates to the use of recombinant techniques to correct genetic deficiencies.

Hemophilia A, a bleeding disorder caused by a deficiency or abnormality of a particular clotting protein, Factor VIII-C, occurs in about 10–20 males in every 100,000. Afflicted individuals suffer episodes of uncontrolled bleeding and are treated currently with concentrates rich in Factor VIII-C derived from human plasma. Recombinant DNA technology has been proposed as useful for providing human Factor VIII-C purified from cultured cells as an alternative treatment for haemophiliacs (Toole et al., 1984, Nature 312:342).

Louis et al. (1988, Proc. Nat. Acad. Sci. USA 85:3150) implanted collagen-embedded mouse primary skin fibroblasts infected with a recombinant retrovirus containing human factor IX cDNA into the epidermis of mice, and detected human factor IX for 10–12 days in the sera.

Garver et al. (1987, Science 237:762) transplanted murine fibroblasts containing recombinant DNA encoding human $\alpha_1$-antitrypsin into the peritoneal cavity of nude mice, and detected human $\alpha_1$-antitrypsin in the sera and the epithelial surface of the lungs. Garver et al. observe that "the level of gene expression in target cells such as fibroblasts has generally been better than with primate bone marrow stem cells".

SUMMARY OF THE INVENTION

In general, the invention features a method of causing production and secretion into the bloodstream of a human patient of a biologically active enzyme for which the human patient suffers a deficiency; the method involves introducing into the human patient donor bone marrow stromal cells which have been transfected with a gene encoding the enzyme, so that the introduced cells can adhere to a bone cavity surface of the patient and produce and secrete the active enzyme.

In preferred embodiments, the transfected gene encodes a lymphokine, a growth factor, or a hematopoietic factor, or another deficient blood-borne protein, such as a coagulation factor, e.g., human Factor VIII-C or anti-Thrombin III. The donor stromal cells are preferably autologous cells, i.e., cells that are genetically identical to the recipient cells, so that immunologic ejection of the engrafted donor cells is minimized; if the donor cells are not autologous, they are preferably similar enough genetically to the recipient to avoid an unwanted immune response; i.e. heterologous cells that are histocompatible, may be used. The use of autologous or histocompatible cells obviates general immune suppression of the recipient.

Preferably, the interaction between the donor stromal cells and the recipient bone is altered to facilitate adherence and stable engraftment by irradiation (preferably X-irradiation) of the recipient bone at the site into which the donor stromal cells are to migrate once they are introduced into the animal. The X-irradiation dosage used is high enough to kill hematopoietic cells, so that the majority of rapidly dividing cells are cleared from the site, and to damage stromal cells at the site, but low enough to avoid death of those stromal cells. The site is preferably a long bone, such as a femur, tibia, or rib.

The invention can be used to treat Factor VIII-deficient hemophilia without eliciting an unwanted immune response to the replenished Factor VIII, because the method of transfer of the Factor VIII gene into the recipient is by autologous transplantation of cells capable of expressing the Factor VIII gene. This is in contrast to other methods or treating hemophilia, which have serious disadvantages. For example, human plasma is both an inefficient and expensive source of Factor VIII, and contains only 100–200 ng/ml of the protein (Fay et al., 1982, Proc. Nat. Acad. Sci. USA 79:7200). The available therapy, although reasonably effective, is very costly and is associated with a high risk of infection. The plasma-derived products currently available are highly impure (<1% Factor VIII) and are commonly produced from pooled plasma lots derived from thousands of donors. These products are associated with a variety of serious complications caused by protein precipitates and are frequently contaminated with adventitious agents such as hepatitis virus and human immunodeficiency virus, the causative agent in acquired immune deficiency syndrome (AIDS). Recombinant Factor VIII, produced by eukaryotic cells transfected with the human Factor VIII-C gene (Wood et al., 1984, Nature 312:330; Toole et al., supra), has not been purified to homogeneity, and, because it may differ from natural human Factor VIII-C in, e.g., glycosylation pattern, may be immunogenic. The invention also advantageously uses stromal-cells, which are long-lived and not rapidly dividing, and are therefore capable, after engraftment, of expressing and secreting the desired enzyme for a prolonged period of time.

Other features and advantages of the invention will be apparent from the following description of the preferred embodiments thereof, and from the claims.

DESCRIPTION OF THE PREFERRED EMBODIMENTS

The drawings will first briefly be described.

Drawings

Correction of Genetic Deficiency

Figure 1A:
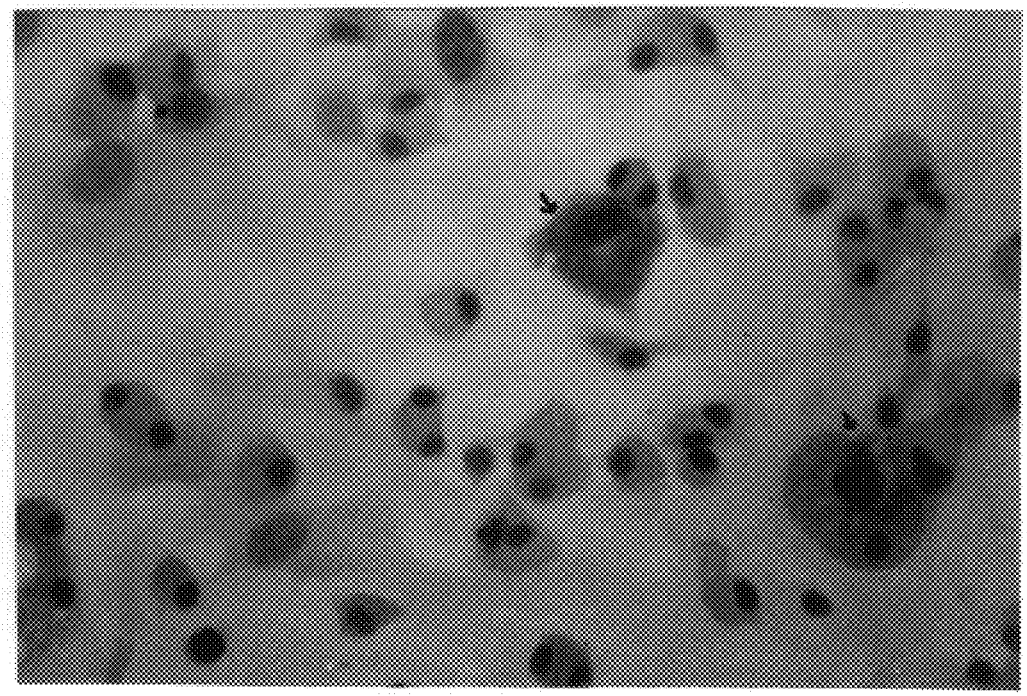
FIG. 1A is a photograph of explanted adherent cells from a transplanted donor mouse at one month after engraftment.

As is discussed above, a human patient suffering from a genetic deficiency disease caused by the absence of a normally functioning enzyme, e.g., hemophilia caused by deficiency of normal Factor VIII C, can be treated, according to the invention by transfecting autologous human stromal cells with a vector containing the human Factor VIII C gene, and then engrafting these transfected stromal cells into a suitably prepared human patient, e.g., a patient who has had irradiation treatment of a target site in a long bone.

Before describing in detail the procedure for treating human hemophilia according to the invention, there will be described, for purposes of enabling some of the techniques employed, an experiment in which neomycin-resistant stromal cells were engrafted into mice; this work is described in the prior art publication Anklesaria et al., (1987) Proc. Nat. Acad. Sci. USA 84, 7681. There will then be described the transfection of murine stromal cells with a gene encoding transforming growth factor-α (TGF-α), followed by the engraftment of those stromal cells into mice; the engrafted cells were found to express and secrete the TGF-α encoded by the introduced gene. Finally, there will be described the procedures by which human hemophilia will be treated according to the invention, beginning with the initial engraftment into mice of Factor VIII gene-containing stromal cells, followed by the engraftment of Factor VIII gene-containing autologous human cells into human patients.

EXAMPLE 1

The Anklesaria et al. Experiments Long-term Cell Cultures

B6D2F1 (C57BL/6J×DBA/2J) mice (Jackson Laboratories, Bar Harbor, Me.) were used to establish long term bone marrow cultures (LTBMC's). The cellular contents of a femur and tibia were flushed into a 25-cm² Corning flask in Fisher's medium (Gibco) supplemented with 25% horse serum (Hazelton) and $10^{-6}$ M hydrocortisone sodium succinate. Fetal calf serum was substituted for horse serum after two weeks. This method has been shown to increase culture longevity (Sakakeeny et al., 1982, J. Nat. Cancer Inst. 68:305). LTBMCs were infected after seven days in culture, and for three consecutive weeks, with viral supernatants containing virus packaged as pure defective virus and 2 ug/ml polybrene (Sigma).

Establishment of a Stromal Cell Line

On day 61 after establishment of LTBMCs, adherent cells from representative LTBMC flasks were removed by treatment with 0.25% trypsin (GIBCO) and replated at either 3×10⁶ or 1×10⁶ cells/25-cm² flask (Falcon) in 8.0 ml Fisher's medium (GIBCO) supplemented with 25% heat-inactivated fetal calf serum (FCS) (Hazelton) and 10⁶ M hydrocortisone sodium succinate, Cultures were maintained at 33° C., 7% $CO_2$, and passaged weekly at the same densities. At passage 8, each of the developing cell lines was plated at limiting dilution and cloned by using penicylinders to separate single-cell derived colonies. Each of the subsequent cell lines was further subcloned twice by limiting dilution. The cell lines were contact inhibited when they reached confluency. All stromal cell lines tested were found to be reverse transcriptase negative, as well as mycoplasma free. Reverse transcriptase activity was measured according to Greenberger, 1984, In: Golde (ed.) Meth. Hematol. 11, N.Y.: Churchill Livingston, p.202, using NIH/3T3 cells as negative controls.

Two clonal murine bone marrow stromal cell lines, GBL/6 and GBL/6 neo$^r$, were developed from continuous bone marrow cultures of B6.cast-GPIA mice (Glu6PI-α, D-glucose-6-phosphate ketol-isomerase; EC 5.3.1.9) mice (Greenberger, 1978, Nature 275:752). The GBL/6 cell line was chosen for these studies because of its endothelial-like characteristics and in vitro support capacity for multipotential hematopoietic progenitor cells.

The stable clonal stromal cell line GBL/6 expresses the α isoenzyme of Glu6PI. The cell line was characterized by staining for alkaline phosphatase, acid phosphatase, peroxidase, α-naphthyl esterase, and lysozyme, as described in Pearse, 1986, Histochem., I, Churchill, London, 3rd ed. Antisera to extracellular matrix proteins laminin, fibronectin (Collaborative Research, Waltham, Mass.), collagen types I and IV, and the alloenzyme marker Glu6PI-α (Charles et al., 1980, Mol. Cell. Biochem. 29:11) were used to identify each protein in the GBL/6 cell line using each specific antiserum and the immunoperoxidase technique of Hadji et al., 1983, Lab. Med. 14:767. GBL/6 cells were fibronectin+, laminin+, and collagen-type IV+, collagen type I−. For immunohistological studies, proximal tibiae were collected, split longitudinally, and fixed for 18 hr in 2% paraformaldehyde/0.1 M cacodylate buffer, pH 7.4. Bones were decalcified in 0.3 M EDTA/0.1 M cacodylate buffer, pH 7.4 for 4 days. Paraffin-embedded bones were sectioned at 5 μm and stained for reactivity with rabbit antiserum against mouse Glu6PI-α and indirect immunoperoxidase staining.

To establish a stromal cell line with a dominant selectable marker, the neomycin-resistance gene, encoding a dominant selectable marker that confers resistance to mammalian cells against the antibiotic G418 (G418$^r$), was transfected on a retroviral vector, first to NIH/3T3 cells and then to cell line GBL/6. Transfection was by calcium phosphate precipitation (Graham et al., 1973, Virol. 52:456). 10 μg of the vector pZIP-Neo(SV)(X) DNA (see below) was used to transfect mouse NIH/3T3 cells. This vector carries the neomycin resistance gene under the control of the SV40 promoter. Clones producing high viral titers were isolated by selecting the transfected cell line with 625 μg/ml of G418 (Gibco), and cloning individual G418$^r$ colonies. Of the cell lines producing defective virus, one was chosen from 19 tested because it produced consistently high viral titers of 3×10⁶ G418$^r$ CFU/ml and used for infection of long-term marrow cultures. This supernatant was named pSVX-neo$^r$ virus. pSVX-neo$^r$ virus was used to infect GBL/6 cells. A subclone, GBLneo$^r$ was selected in 500 μg/ml G418 and expanded in vitro. GBL/6-neo$^r$ cells had cytochemical properties and extracellular matrix proteins indistinguishable from those of GBL/6 cells.

GBL/6 cells support growth in vitro of hematopoietic stem cells forming colony-forming units of spleen cells (CFU-S) and of granulocytes, erythrocytes, and macrophage/megakaryotcytes (CFU-GEMM) in the absence of detectable growth factors, e.g., interleukin 3 (multi-colony stimulating factor), granulocyte macrophage colony-stimulating factor, and granulocyte-stimulating factor.

The hematopoietic support capacity of GBL/6 cells or GBL/6-neo$^r$ cells in vitro could not be attributed to the synthesis of detectable quantities of any known hematopoietic with multi-CSF activity.

Total cellular RNA isolated from the GBLneo$^r$ stromal cell line was used to prepare poly(A)$^+$mRNA by a modification of the guanidine hydrochloride extraction method (Maniatis et al., 1982, Molecular Cloning: A Lab. Manual, Cold Spring Harbor Lab., Cold Spring Harbor, N.Y.). Specific message for interleukin 3 (IL-3) (Fung et al., 1984, Nature 307:233), granulocyte/macrophage. colony-stimulating factor (GM-CSF) (Gough et al., 1984, Nature 309:763), macrophage colony-stimulating factor (M-CSF) (Kawasaki et al., 1985, Science 230:291), IL-1 (Auron et al., 1984, PNAS 81:7907), and granulocyte colony-stimulating factor (G-CSF) (Isuchiya et al., 1986, PNAS 83:7633) was identified by hybridization with specific cDNA probes (>108 cpm/μg) as described in Maniatis et al., ibid. mRNA from GBL/6-neo$^r$ cells was analysed by RNA blot hybridization for poly(A+) mRNAs of known growth factors. GBL/6-neo$^r$ cells had no detectable poly(A+) mRNA for IL-3, GM-CSF, G-CSF, or IL-1, and did have detectable mRNA for M-CSF. GBL/6 cells produced macrophage colony-stimulating factor constitutively. The support capacity of the GBL/6 cell line may be due either to the ability of M-CSF to trigger release of other CSFs from accessary cells in vivo and in vitro or to another growth factor.

Assays for Hematopoietic Cells

Adherent and nonadherent cells were removed from LTB-MCs weekly and assayed in vitro for colony forming ability CFU-GEMM with and without G418 (Johnson et al., 1977, Proc. Nat. Acad. Sci. USA 74:3879; Nakahata et al., 1982, Proc. Nat. Acad. Sci. USA 79:3843). The biological activity of each lot of G418 was assessed in colony assays on uninfected cultures. All G418 concentrations reported are in actual weight per milliliter. Progenitor cell assays were done in medium containing 10% BSA (bovine serum albumin), 30% FBS (fetal bovine serum), $10^{-2}$ M 2-mercaptoethanol with methylcellulose as a semisolid base, and supplemented with three conditioned media: (CM) WEHI-3BCM (Ihle et al., 1983, J. Immunol. 131:282), L-cell CM as a source of macrophage colony-stimulating factor (M-CSF) (Stanley et al., 1977, J. Biol. Chem. 252:4305) or 10% pokeweed mitogen-stimulated spleen cell CM and 2.0 μm/ml EPO (erythropoietin) (Humphries et al., 1979, Blood 53:746).

In vivo CFU-S assays were done as described by Till and McCulloch (1961; Radia. Res. 14:213). For each group, 5–10 mice were irradiated to 1000 rad, 140 rad/min (cesium source), and injected with $5\times10^5$ cells/mouse. Mice receiving no progenitor cells died within 12 days of irradiation and had ≤0.1+0.3 endogenous colonies per spleen.

Engraftment of GBL/6-neo$^r$ Cells into Mice

Figure 1B:
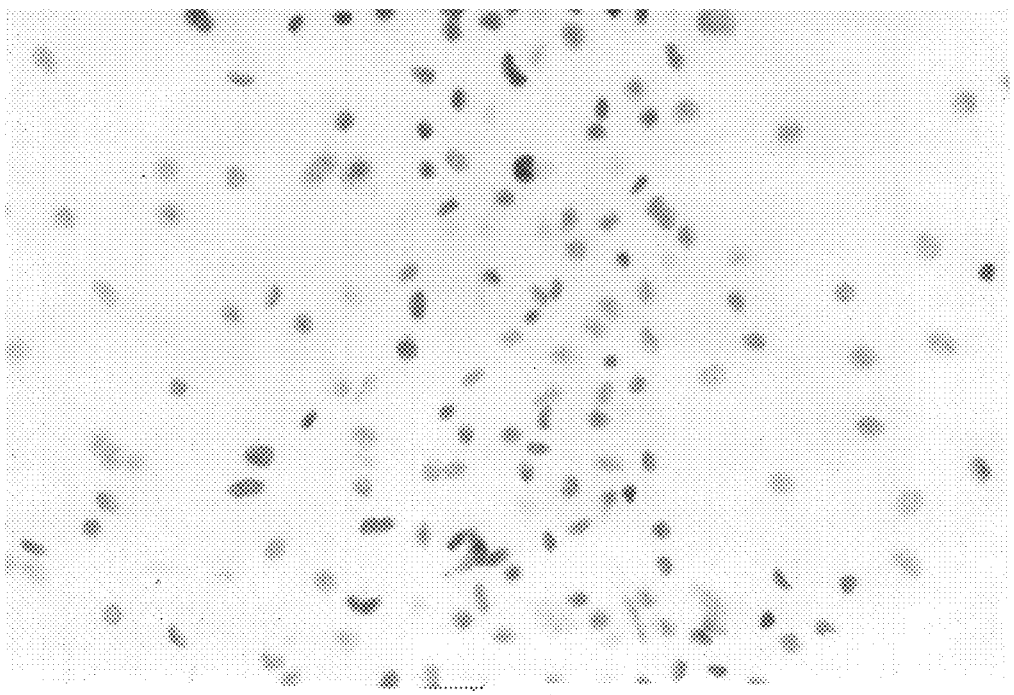
FIG. 1B is a photograph of explanted cells from a non-transplanted-irradiated mouse.

The ability of injected stromal cells to home and stably seed into marrow sinuses in vivo was first evaluated by in vivo immunohistochemical technique. Glu6PIα$^+$ stromal cells were identified in situ two months after transplant in the RHL marrow sinuses of transplanted mice. Two months after transplantation, neither engrafted nor irradiated nonengrafted control mice demonstrated detectable donor-originating Glu6PI-α cells in spleen, liver, lung, or peritoneal washings. As shown in Table 1, 1 month after transplantation, 26.2% of the adherent stromal cells in marrow cultures explanted from transplanted mice were of donor origin. Adherent stromal cell explants were established, and donor-originating stromal cells were identified at day 18 using specific antiserum against Glu6PI-α alloenzyme marker (Charles et al., 1980, Mol. Cell. Biochem. 29:11), and immunoperoxidase staining (PAP). These cells are illustrated in FIG. 1, upper panel, which shows adherent marrow cells explanted in vitro from the RNA of transplanted mice at 1 month after transplantation. FIG. 1, lower-panel, shows marrow cells explanted in vitro from control irradiated but non-transplanted mice at 1 month. Donor originating cells were identified in vitro using specific rabbit antiserum against murine Glu6PI-α and immunoperoxidase staining. The arrow shows a positive staining cell. Table I also shows that the highest percentage of donor-originating cells was 82.5% and 62.5% of total adherent cells in marrow explants 2 and 3 months, respectively, after transplanation. Glu6PI-α cells composed 78% of adherent cells in LTBMCs established from RHLs (13-Gy irradiated) of transplanted mice. Adherent stromal cells from day-70 LTBM's were trypsinized, replated on coverslips, and processed for PAP (immunoperoxidase staining). The percentage of donor-originating Glu6PI-α$^+$ cells was <0.01% in the nonadherent cells and in individual CFU-GEMM colonies derived from these LTBMCs. In contrast, nonadherent hematopoietic progenitor cells harvested from these same LTBMCs had no detectable Glu6PI-α cells. No detectable Glu6PI-α stromal cells were identified in situ or in LTBMCs from control-irradiated nontransplanted mice (FIG. 1, lower, Table 1).

The recovery of donor-originating GBLneo$^r$ cells in cultures explanted from control-irradiated nontransplanted mice and mice transplanted with GBLneo$^r$ cells were selected for growth in the presence of G418 (500 ug/ml) Mice were transplanted with $5\times10^5$ GBlneo$^r$ cells per mouse as described above. Two months after transplantation the total number of cells recovered were as follows: $5.8\times10^6$ per RHL (13 Gy) and $8.6\times10^6$ per left hind limb (3 Gy) from control irradiated nontransplanted mice; $6.5\times10^6$ per RHL (13 Gy) and $6.9\times10^6$ per left hind limb (3 Gy) from transplanted mice. Adherent stromal cell explants were established with $5\times10^6$ cells per dish (60×10 mm). Some were fed biweekly with G418 (500 μg/ml). The number of G418-resistant colonies were scored 17 days after cultures were established in vitro. Table 2 shows that G418 resistant stromal cell colonies were found in the explanted RHL marrow of transplanted, but not of control-irradiated mice. Values in parentheses represent percent control G418-resistant colonies calculated as the number of G418-resistant stromal cell colonies per $5\times10^6$ cells by the total number of stromal cell colonies per $5\times10^6$ cells×100.

The physiological function in vitro of transplanted GBL/6 stromal cells was evaluated. At monthly intervals LTBMCs were established individually from each hind limb of GBL/6-transplanted or irradiated-nonengrafted control mice. The functional integrity of the adherent stromal cells was quantitated by measuring the longevity of hematopoiesis as cumulative number of total nonadherent cells and multipotential progenitor cells produced over 70 days in vitro. The cumulative number of viable nonadherent cells produced per culture of marrow established at 1, 2, and 3 months after transplant from the RHL of mice transplanted with GBL/6 cells was higher than that produced by cultures from irradiated, nontransplanted control mice. The cumulative number of multipotential hematopoietic progenitor cells forming mixed CFU-GEMM colonies, using procedures described below, per RHL culture (13 Gy), established at 1, 2, and 3 months from transplanted mice was $30.5+/-3.7\times 10^2$, $45.6+/-2.5\times10^2$, and $34.7 +/- 4.2\times10^2$, respectively, compared with $5.13 +/- 2.2\times10^2$, $7.3 +/- 0.9\times10^2$, and $6.04 +/- 0.13\times10^2$ for control irradiated, nontransplanted mouse marrow cultures (P<0.05).

The effect of donor stromal cell number on recovery of hematopoiesis in irradiated mice was tested. Mice were innoculated with $1\times10^6$, $5\times10^5$, or $1\times10^5$ cells. Long-term bone marrow cultures were established 2 months after GBL/6 cell transplantation. Viable nonadherent cells produced per flask over..70 days were quantitated, as were CFU-GEMM from each RHL (13 Gy) or LHL (3 Gy) culture. A detectable chimeric stromal cell population was established with a minimum of $1\times10^5$ stromal cells.

Production of hematopoietic progenitor cells by RHL cultures from transplanted mice reached 48% of the level seen in cultures from nonirradiated mice compared with 5% in marrow cultures from irradiated nontransplanted mice. An X-ray dose of 3 Gy to the left hind limb decreased hematopoietic stem cell production in marrow cultures from irradiated nontransplanted mice to 35% compared with cultures from nonirradiated mice. However, GBL/6 cell engraftment did not detectably increase cell production in LTBMCs from limbs irradiated at this dose.

The efficiency of repopulation of marrow sinuses of the RHL (13 Gy) by endogenous CFU-S and the recovery of peripheral blood counts was next measured in GBL/6 cell-transplanted and in irradiated nontransplanted control mice. Groups of C57BL/6J mice were irradiated in 2-Gy increments from 3 Gy to 7 Gy with the RHL receiving between 10 and 12.5 Gy, as shown in Table 3. Each irradiation group had 5–10 mice per group. All mice received an additional 10–12.5 Gy to the RHL. One group was injected with $5 \times 10^5$ GBl/6 stromal cells per mouse. Values in parentheses are from the group that received no cells but were control irradiated. Six weeks after irradiation and transplantation, a subgroup from each group was sacrificed; cells were flushed from each RHL and assayed for CFU-S. Results are expressed as mean±SD of three to five mice. An average of 4.4±2.9 endogenous CFU-S colonies was seen on the spleens of irradiated noninjected mice. A subgroup from each irradiation dose group was injected with $5 \times 10^5$ GBL/6 cells per mouse. Six weeks after irradiation and transplantation, the RHL from each animal in each dose group was assayed for the number of multipotential stem cells forming CFU-S. Results are expressed as mean±SD of at least three mice per group. Nonirradiated mice had a white blood cell (WBC) count of $8.8 \pm 1.6 \times 10^3/mm^3$, platelet (PLT) count of $173.7 \pm 28.7 \times 10^3/mm^3$ and erythrocyte (RBC) count of $7.8 \pm 0.05 \times 10^6/mm^3$.

As shown in Table 3, at lower TBI doses of 3 and 5 Gy, the number of CFU-S-forming multipotential stem cells per RHL was similar in GBL/6 transplanted and in control irradiated nontransplanted mice. In contrast, sublethally irradiated (7-Gy TBI) mice transplanted with GBL/6 cells showed a significantly higher number of stem cells forming CFU-S in the RHL compared with the number recovered from the RHL of irradiated nontransplanted control mice ($P<0.01$ compared with values from control irradiated non-transplanted mice.)

The kinetics of recovery of peripheral blood counts in mice after TBI doses of 3 or 5 Gy were similar in transplanted and control irradiated nontransplanted mice. In contrast, a significant recovery of peripheral blood white blood cell count ($6.9 \pm 1.0 \times 10^3$) and platelet count ($112.5 \pm 2.5 \times 10^3$ per $mm^3$) was seen in 7-Gy-irradiated GBL/6-transplanted mice compared with irradiated nontransplanted controls (white blood cell count: $4 \pm 0.05 \times 10^3$ cells per $mm^3$; platelet count 50±3 platelets per $mm^3$; $P<0.05$; Table 3).

The data show that previous irradiation damages the stromal cells of the hematopoietic environment and suggest that niches, freed of endogenous hematopoietic stem cells by the higher dose, provide more efficient seeding sites for injected donor cells.

Expression of the TGF-α Gene in Mice Homing of Hematopoeitic Cells to Irradiated Site A defective retroviral vector containing a TGF-α cDNA was transfected by electroporation into the hematopoiesis-supportive bone-marrow stromal cell line GBL/6, which was shown, in Anklesaria et al., above, to be capable of engrafting in vivo to a high dose irradiated site in the syngeneic mouse. The engrafted TGF-α-transfected GBL/6 cell line (Gp-TGF$_\alpha$) was found to remain stably associated in the irradiated sites for many months and to produce the ligand TGF-α, a growth factor having functional homology to epidermal growth factor (EGF), and to the same receptor.

The ability of an IL-3 dependent hematopoietic 1 progenitor cell line (32DC13) to engraft and proliferate on the Gp-TGFα cell line in vitro was shown by transfecting 32DC13 with a eukaryotic expression vector containing both the selectable gene (E. coli-gpt) and the gene encoding the EGF-receptor (EGFR). Expression of the EGFR gene resulted in the activation of a mitogenic signal in response to EGF (see Pierce et al., Science, 1988, 239:623). Control nontransfected 32DC13 cells, co-cultivated with either the Gp-TGFα cell line or GBL/6, did not proliferate or form cobblestone areas. The EGFR-transfected 32DC13 cells (32D-EGFR) proliferated extensively on Gp-TGFα cells, but not on GBL/6 cells, for over 7 weeks in vitro. In contrast, hematopoietic progenitor cells from LTBMCs proliferated and produced CFU-GEMM progenitor cells more effectively with GBL/6 cells than with Gp-TGFα cells. Thus only cells that could form a receptor/ligand interaction were able to engraft and proliferate extensively in vitro. These results are shown in Table 4.

The ability of 32D-EGFR to home to in vivo engrafted Gp-TGFα stromal cells was tested. Irradiated C57BL/6J mice were transplanted with $5 \times 10^5$ Gp-TGFα cells/mouse. Two months after transplantation, mycophenolic acid resistant 32D-EGFR cells ($1.0 \times 10^7$ cells/mouse) were injected into Gp-TGFα transplanted and control irradiated nontransplanted mice. Donor origin, neo$^r$ TGF-α producing colonies (11.5±2.5 CFU-F/limb) were detected in marrow explants from irradiated Gp-TGFα transplanted, but not from control irradiated non-transplanted mice. 32D-EGFR $15.2 \pm 8.0 \times 10^5$ cells/limb were recovered from hind limb explants of irradiated Gp-TGFα transplanted mice, compared to $0.55 \pm 0.10 \times 10^5$ 32D-EGFR cells from hind limb explants of irradiated nontransplanted control mice. These data indicate that marrow stromal cells containing a transfected enzyme-encoding gene became established in the irradiation-prepared bone cavity, and expressed the enzyme following engraftment.

Treatment of Factor VIII Deficiency in Humans Human Factor VIII-C Gene

Figure 3:
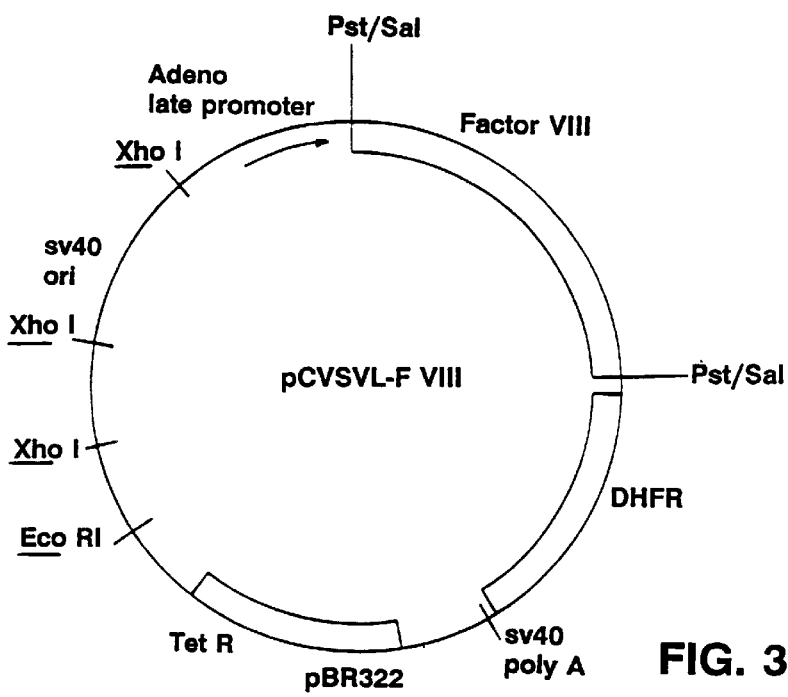
FIG. 3 is a diagrammatic representation of a retroviral vector containing the human Factor VIII gene.

The human coagulation Factor VIII-C gene from the cDNA clone pSP64-VIII (Toole et al., 1984, supra) can be introduced into any suitable mammalian expression vector, e.g., the vector pCVSVL, and expressed in human stromal cells (gene expression in pCVSVL is described in Kaufmann et al., 1982, Mol. Cell. Biol. 2.1304; Clark et al., 1984, Proc. Nat. Acad. Sci. USA 81:2541). The DNA sequence of the coding region of the human Factor VIII-C gene is given in Wood et al., 1984, supra, hereby incorporated by reference. The Factor VIII-C gene can be cloned into the PstI site of pCVSVL by excising the gene on a SalI fragment and using synthetic oligonucleotide adapters containing SalI cohesive ends, as described in Toole et al., supra. The Factor VIII-C gene in pCVSVL-FVIII will be under the control of the adenovirus major late promoter, as shown in FIG. 3. This plasmid also includes the SV40 polyadenylation site (SV40 poly A), a duplicated SV40 origin of replication (SV40 Ori), and a deletion in pBR322 that enhances replication of such plasmids in animal cells (Lusky et al., 1981, Nature 293:79). Selectable genes in the vector are those encoding tetracycline resistance (Tet$^R$) and mouse dihydrobolate reductase (DHFR). Similar Factor-VIII-C mammalian cell expression vectors are described in detail in Kaufman et al. WO87/04187, pub. Jul. 17, 1987, hereby incorporated by reference.

Assay for Factor VIII Activity

Factor VIII-C activity in culture supernatants can be determined by the Kabi Coatest Factor VIII-C method, modified to afford a sensitivity better than 0.05 mU/ml, and by the one-stage activated partial thromboplastin time (APTT) coagulation assay (Lee et al., 1983, Thromb. Res. 30:511) using Factor VIII-C-deficient plasma. The Coatest assay is based on the activation of natural Factor X by Factor IXa; Factor IXa is dependant on Factor VIII. The APTT assay is based on the marked increase in the coagulation activity of Factor VIII in the presence of thrombin. For thrombin activation, samples can be pretreated 1–10 min. with 0.2 units/ml thrombin at room temperature. Alternatively, Factor VIII can be quantitated by radioimmunoassay, using an antibody specific for Factor VIII, as described in Wood et al., 1984, supra.

Transfection of Murine Cells With the Factor VIII-C Gene

A vector containing the human Factor VIII-C gene and the $neo^r$ marker gene can be used to transfect murine stromal cells (e.g., containing GBL/6 cells) by electroporation, retroviral vector transfer, or any other suitable conventional vector transfer technique.

Subclonal lines of GBL/6 $neo^r$ cells expressing detectable levels of human Factor VIII-C will be selected in vitro by persistence of neomycin resistance, and production in serum-free conditioned medium of those subclones of detectable human Factor VIII-C by western blot analysis or biochemical assay.

Engraftment Into Irradiated Mice

C56BL/6J male mice will be used as recipients. The cells of these animals have three "recipient" markers: Y-chromatin, the beta variant of glucose phosphate isomerase (GPIA), and absence of detectable neomycin resistance activity. Donor origin cells will be derived from the GBL/6 $neo^r$ VIII-C-1 clonal line, and have four markers of donor origin: absence of detectable Y-chromatin, detectable immunoperoxidase staining with hetero-antiserum to GPIA, biological neomycin resistance in vitro, and detectable production of human Factor VIII-C. A dose response curve for engraftment of these cells into irradiated mice will be carried out as follows.

Recipient mice will receive 300 cGy total body irradiation (TBI) and 1000 cGy irradiation to the isolated right hind limb (RHL), delivered by a $^{137}Cs$ γ cell 40 irradiator. The day after irradiation, animals will be injected intravenously by tail vein with a single cell suspension of $1 \times 10^4$, $5 \times 10^4$, $1 \times 10^5$, or $5 \times 10^5$ of a high producing GBL/6 $neo^r$ VIII-C clonal line (cells from 10 mice pooled per group). The mice will then be returned to their cages and monitored weekly for detectable Factor VIII in the plasma. Representative mice will be sacrificed and plasma removed by cardiac puncture at different timepoints and assayed by Western blot analysis for human Factor VIII-C, which will be distinguishable from mouse Factor VIII-C by its specific reactivity with monoclonal anti-human VIII-C antiserum (available from several public sources).

At the time of sacrifice of the mice of each dose grace, nucleated cells will be removed from the right and left hind limbs of each animal and used to set up murine continuous bone marrow cultures, as described above. Bone marrow cultures from the right hind limb will be expected to contain a higher percentage of donor origin, neomycin resistant, stromal cells and continuous marrow cultures from this limb would be expected to produce detectable human Factor VIII-C in vitro. Timepoints for explant of marrow from engrafted mice will be chosen at one week, two months, four months, and six months after stromal cell transplantation as well as at other intermediate timepoints. Plasma levels of human Factor VIII-C will be measured and the level of Factor VIII-C produced over time will be graphically displayed. The optimum number of stromal cells transplanted will be determined in relation to the highest level of Factor VIII-C production in one hind limb.

Irradiation Dosage Testing

If human Factor VIII-C is not detectable in the mouse plasma after reconstitution of one hind limb with donor cells after high dose irradiation of that limb, a sequential "niche" preparation protocol can be used to irradiate both hind limbs and prepare a larger niche for engraftment. This approach has been used to detectably change the macrocytic anemia of the $S1/S1^d$ strain of mice in order to achieve a greater percentage of total marrow volume replacement by donor stromal cells. This strain contains a genetic defect in the bone marrow microenvironment resulting in a deficiency of mature erythroid precursors and reduced numbers of pluripotential hemopoietic stromal cells.

A dominant fraction of the marrow microenvironment of $S1/S1^d$ mice was replaced by preparing the mice with either 2 Gy TBI and 20 Gy to both hind limbs (BHL, single schedule) or by sequential irradiation transplantation (multiple schedule). Adult recipient $S1/S1^d$ mice received 1–2 Gy TBI and 10.0–20.0 Gy, to the right-hind-limb (RHL) or both hind limbs (BHL) delivered by a linear accelerator as described in Anklesaria et al., 1987, supra. 1 Gy TBI and 10 Gy x-ray doses are preferred due to the relative sensitivity of $S1/S1^d$ mice to TBI. Irradiated mice were transplanted with $5 \times 10^5$ stromal cells ($GBLneo^r$) by intravenous injection (single schedule). For sequential boost irradiation-transplantation studies with $S1/S1^d$ mice, 1 Gy TBI and 10 Gy to the RHL was delivered by linear accelerator on day 0. A single cell suspension of the $GBLneo^r$ cell line was injected intravenously 48 hours later. Two months after the first irradiation schedule, the same group of mice received 1 Gy TBI and 10 Gy to the left hind limb (LHL). Another injection of the $GBLneo^r$ cell line was administered 48 hours later (multiple transplant schedule). Control irradiated nontransplanted mice received 2 Gy TBI and 10 Gy to both hind limbs (BHL).

Figure 2:
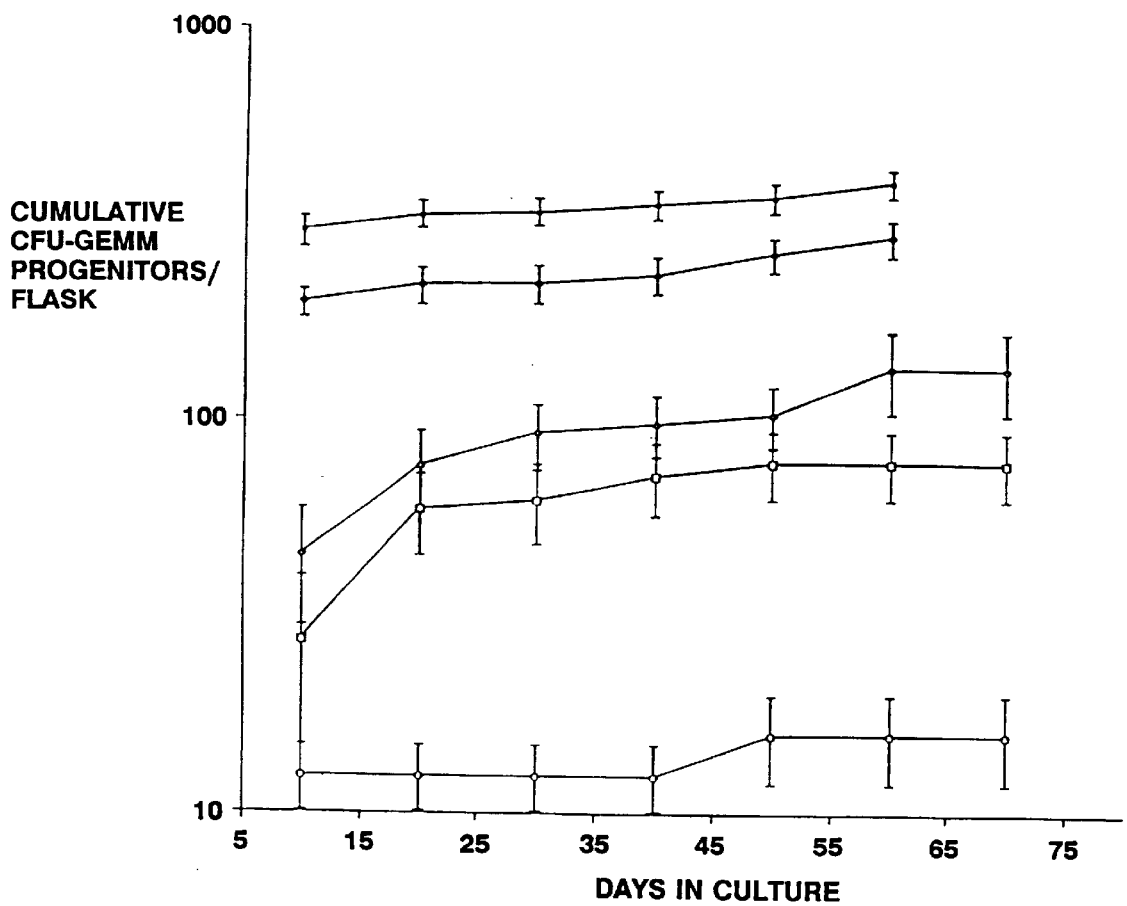
FIG. 2 is a diagram of hematopoietic progenitor cell growth from LTBMCs established from S1/S1$^d$ mice.

None of the control irradiated nontransplanted mice survived. LTBMCs established from $GBLneo^r$ transplanted mice (2 Gy TBI and 20 Gy BHL) at 5 months showed increased cumulative CFU-GEMM forming progenitors/flask in both right (298.8±32.7) and left (415.8±36.5) hind limb cultures compared to nonirradiated $S1/S1^d$ mice (p<0.05, FIG. 2). At two or four months after irradiation-transplantation LTBMCs were established from 3 mice/group. In separate experiments, two months after mice received the second irradiation-transplantation, the cumulative number of CFU-GEMM forming progenitors obtained per flask was higher in LTBMCs established from engrafted right (136.1±32) and left (78.6±15.4) hind limbs of $GBLneo^r$ transplanted mice compared to those from control non-irradiated $S1/S1^d$ mice (p<0.05, FIG. 2). In FIG. 2, the symbols for cells from control non-irradiated mice are open circles; from $GBLneo^r$ transplanted RHL-20 Gy mice are open boxes; from GBLneo$^r$ transplanted LHL-20 Gy mice are closed triangles; and from GBLneo$^r$ transplanted LHL-10Gy are closed boxes.

Thus, in S1/S1$^d$ mice, high dose irradiation may help create a "niche" in the marrow cavity to support transplanted stromal cells, and may also eliminate endogenous stromal cells that suppress hemopoiesis.

Quantitation of Cells and Enzyme Level

The number of donor stromal cells engrafted in vivo will be quantitated by the colony assay for neomycin resistant stromal cells described above. This assay is carried out by plating explanted nucleated marrow cells to petri dishes in the presence of a concentration of 100 ug/ml G-418 and scoring of >50 cell colonies at day 7, following plating of the cells at serial ten-fold dilutions to a limiting dilution.

In order to quantitate the level of production of human Factor VIII-C relative to the number of engrafted stromal cells, the number of colony-forming stromal cells engrafted will be determined as described above and the levels of human Factor VIII-C detectable in vivo and in vitro following explant will be determined, also as described above. These experiments will demonstrate detectable human Factor VIII-C in vivo in mice with persistent levels for over six months.

The following procedures were designed to demonstrate that hemophilia-A can be corrected in vivo in humans using a stromal cell engraftment protocol similar to that described above for the murine system. The recipient will be prepared with a similar high dose irradiation technique.

Long-Term Human Bone Marrow Cultures

Nucleated marrow cells from patients with hemophilia-A who have previously contracted human immunodeficiency virus infection from HIV-contaminated plasma derivatives will be explanted after informed consent has been obtained. These marrows will be established in human continuous bone marrow culture using a technique for preparation of suitable medium supplemented with hydrocortisone sodium hemisuccinate.

Marrow from patients to receive transplant will be aspirated from iliac crests removing approximately 3×10$^8$ nucleated cells. The bone marrow harvesting technique is as described by Buchner et al., 1984, Blood 64:630, hereby incorporated by reference, and Thomas et al., 1970, Blood 36:507, as modified by Jin et al., 1985, Exp. Hematol. 13:879, hereby incorporated by reference.

Briefly, inoperatively obtained bone marrow specimens from hip surgery are purified free of spicules by mincing with scissors in McCoy's 5A medium, and then single-cell suspensions are prepared by drawing the marrow through progressively smaller gauge needles to a 30-gauge needle. Cultures are established by inoculation of 3×10$^7$ to 4×10$^7$ nucleated marrow cells to each Corning 25-cc plastic flask in McCoy's 5A Medium Supplemented as previously described (Greenberg et al., Blood 58:72, 1981), and containing 12.5% heat-inactivated fetal calf serum, 12.5% heat-inactivated horse serum and 10$^{-6}$ mol/L hydrocortisone. Cultures are incubated at 33° C. and left undisturbed for 7 to 14 days; this time is absolutely required for adherence of hematopoietic stromal cell islands that are associated with long-term hematopoiesis. After this initial incubation, all nonadherent cells are recovered by aspiration, and a Ficoll-Hypaque density cut is performed to remove red blood cells. All nucleated cells are then returned to the individual culture flasks in fresh medium. Cultures are then fed twice per week for the first four weeks, and, thereafter, once per week by removal at each feeding of all medium and nonadherent cells and replacement of 8.0 mL fresh medium. The human stromal cells will then be transfected as described above for murine cells, with a vector containing the human Factor VIII-C gene by electroporation, retroviral vector transfer, or any other suitable technique.

The number of stromal cells transfected and expressing Factor VIII-C gene will be quantitated by either linkage of the Factor VIII-C gene to a neomycin resistance gene and selected for neomycin resistant colonies, or by subcloning lines in culture and assaying their supernatents for detectable levels of Factor VIII, as described above, or by staining the cells for detectable Factor VIII-C production by immunoperoxidase technique using monoclonal antibody to human Factor VIII-C. A vector transfection system will be chosen which gives a maximum frequency of expression of transfected stromal cells with the VIII-C gene. When the vector pZIP-NecSV(X), carrying the neomycin resistance gene, is transfected into fresh human stromal cells, neomycin resistance is stably expressed in vitro in approximately 10–15% of cells which are normally sensitive to the neomycin analog G418. Based on this neo-experiment at least 10% of human stromal cells will be expected to stably express the Factor VIII-C gene. If lower numbers are detected, cloned permanent. immortalized human bone marrow stromal cell lines, KM101, KM102, KM103, KM104, and KM105 will be used (Fitzgerald et al., 1988, Int. J. Rad. Oncol. Biol. Phys. 15:1153) to maximize the likelihood of transfection and detection of the Factor VIII-C gene in vitro. Factor VIII-C production will be quantitated in the clonal lines and compared on a per cell bases with that detected in the GBL/6 neo$^r$ mouse line. Toxicology and tumorigenicity studies will be performed as follows.

Growth of human stromal cell lines in vitro is associated with potential problems, including activation of Epstein-Barr virus (Rothstein et al., 1985, Blood 65:744), contamination of the stromal cells with pathogens during in vitro culture, including mycoplasma, bacterial or fungal infection, and spontaneous transformation to tumor-inducing lines. Microbial contamination of the stromal cultures will be monitored by bacteriological, virological and mycoplasma assays of material. The cells will be tested for Epstein-Barr virus nuclear antigen as described in Rothstein et al, supra, and will be screened by electron microscopy to determine whether there is any evidence of Epstein-Barr virus activation. EBV has never been detected in human bone marrow stromal cells prior to 20–25 weeks of continuous in vitro cultures. The mechanism of activation of EBV is not known but is detected at low frequency in control human marrow cultures.

To determine whether spontaneous tumorigenicity has evolved following insertion of the Factor VIII-C gene, stromal cell cultures expressing Factor VIII-C will be engrafted at 1×10$^7$ cells IP, IV, or intrathecally, into nude mice. These animals will be monitored for six months to determine whether tumors are detected. Positive controls for these experiments in nude mice will include human tumor cell lines HL60 and U937 (Greenberger et al., 1978, Cancer Res. 38:3340). Using these criteria, it will be possible to detect evidence of tumorigenicity of human marrow stromal cells expressing Factor VIII-C; 10% and possibly as high as 50–60%, of freshly explanted human stromal cells may express the transfected Factor VIII-C gene.

Patient Preparation

Each patient will be prepared for autologous engraftment of his own Factor VIII-C transfected stromal cells by irradiation of one iliac crest. A radiation therapy portal of no greater than 10 cm. wide×10 cm. long will be chosen to incorporate the iliac crest and part of the ischium, unilaterally shielding bladder and rectum, or an angled AP-PA portal will be chosen to minimize the volume of intestine, bladder, and other normal soft tissues in the field. A single fraction size of 1000 cGy will be delivered to this segment of bone marrow by AP-PA or opposed oblique technique. Fractionated radiotherapy may be more suitable and perhaps more easily tolerated by humans to prepare a high dose irradiated niche. Basic human radiation biology parameters suggest that 500 cGy daily for two days, or 300 cGy daily for ten days, should produce an isoeffect equivalent to 1000 cGy in one fraction (see Fletcher, ed., Textbook of Radiotherapy, 1980, 3rd ed., Lee and Febinger, Phila. Chp. 2, pp. 180–219). (1000 cGy delivered to a single iliac crest would be expected to produce no untoward effects, and is commonly used in palliative radiotherapy of a single bone having painful metastasis. The day after single fraction irradiation of the iliac crest, patients will receive intravenous infusion of a single cell suspension of autologous marrow stromal cells expressing the human Factor VIII-C gene. The patient s plasma will then be monitored weekly for detectable human Factor VIII-C levels.

Variations in Protocols

It is expected that human factor VIII-C production by engrafted autologous stromal cells will be detectable if the chosen infected number of $1 \times 10^8$ cells is adequate to selectively seed into the high dose irradiated niche. If Factor VIII-C is not detected in the plasma, it will be necessary to determine whether adequate seeding of the irradiated site has been achieved.

Patients will be monitored for in vivo seeding by indium oxine labelling of the donor stromal cells prior to engraftment. A gamma camera whole body scan will be carried out 24 hours after engraftment to determine whether the cells have preferentially seeded to the high dose irradiated bone. Assays carried out in the murine model have already demonstrated that the high dose irradiated limb preferentially takes up the infected stromal cells and that the indium label is stable for 48 hours. Doses of indium oxine will be used similar to those used in nuclear medicine lymphoscintogram scanning techniques for lymphocyte homing in Hodgkin's disease, and in red cell sequestration studies for patients with myeloid metaplasia and myelofibrosis.

If Factor VIII-C levels are initially detected in the plasma but then decrease rapidly, it will be determined whether cell graft instability or vacum expression instability is the cause of this failure. Vector instability can be corrected by standard methods, i.e., replacing or modifying the vector for expression of the Factor VIII-C gene in vitro; any modifications will use data derived from work carried out with fresh explanted human marrow or clonal human marrow stromal: cell lines. Graft instability may be determined by in vivo studies using $S^{35}$ labelled human marrow stromal cells that have been engrafted in vivo and watched for 100 days, which is equal to the half-life of $S^{35}$. Detectable $S^{35}$ in the high dose irradiated bone initially should be followed by persistent detection in that high dose region for 100 days; a decrease in detectable $S^{35}$ by scanning would suggest instability of cells in the graft site. If this were to occur, other methods for preparation of the niche could be use,, although it is expected that the graft will be adequately seeded and stable after 1000 cGy.

Failure to detect adequate levels of Factor VIII-C despite adequate engraftment of stromal cells to the high dose irradiated bone and stable vector expression may be associated with an inadequate relative number of stromal cells. This problem may be corrected by preparation of several niches similar to that which was required in the $S1/S1^d$ mouse mutant model. According to this methodology, both iliac crests or one iliac crest and one femur will be prepared as larger niches using the same high dose irradiation scheme, fractionated irradiation scheme as described above. Single or multiple inoculations of donor stromal cells each transfected and expressing Factor VIII-C from human marrow cultures will then be carried out.

Alternate Methods for Introduction of Factor VIII-C Gene Into Human Stromal Cells Viral vectors containing the Factor VIII-C gene can be introduced into human stromal cells either by infection or by transfection. The recombinant viral DNAs can be propagated the presence of an appropriate helper virus and packaged into infectious virions, or can be propagated in a packaging-defective viral producing strain. Infectious virus can be produced from, e.g., mouse a NIH/3T3 or $\psi_2$ cell line which has been transfected with recombinant viral DNA. Cells can be crown as described in Cepko et al., 1984, Cell 37:1057, and infections performed in the presence of 8 $\mu$g/ml polybrene (Sigma).

Retroviruses, comprising single-stranded RNA molecules, can be used for viral infections; their RNA's are converted intracellularly into double-stranded proviral DNAs, which are integrated into the host genome after duplication of one of the termini of the viral sequence to generate the long terminal repeats (LTR). Helper-free stocks of recombinant retrovirus are produced in helper cell lines after transfection with a recombinant retroviral vector. The helper cell lines contain an integrated copy of the retroviral genome. The provirus provides all the trans-acting functions necessary for replication and encapsidation of a recombinant genome, but is defective in the ability to encapsidate its own RNA.

SV40 derived plasmid vectors can replicate extrachromosomally in monkey COS cells (Gluzman, 1981, Cell 23:175). Vectors that can replicate autonomously in a variety of eukaryotic cells (e.g., human monkey, dog) are described in Pouwels et al., eds., "Cloning Vectors", 1985, Elsevier Sci. Pub., B.V., hereby incorporated by reference. Vectors without a replicon for animal cells usually have a replicon for E. Coli. Such vectors, also described in Pouwels et al., cannot replicate extrachromosomally in animal cells; transformants can be isolated only if they integrate into the host genome and express a selectable marker. A detailed description of animal cell vectors can be found in Rigby, 1983, J. Gen. Virol. 64:255; Elder et al., 1981, Ann. Rev. Genet. 15:295; and Subramani et al., 1983. Anal. Biochem. 135:1.

Selection of stable transformants can be carried out using a number of genetic markers, e.g., the E. coli gpt gene encoding resistance to mycophenolic acid, the neo gene from TN5 encoding resistance to the antibiotic G418, the dhfr sequence from murine cells or E. coli which changes the phenotype of DHFR⁻ cells into DHFR⁺ cells, and the tk gene of herpes simplex virus, which make TK⁻ cells phenotypically TK⁺ cells.

Stable human stromal cell lines can be constructed that efficiently express the gene of interest by placing the gene under the control of a strong promoter, e.g., the early and late promoters of SV40 ($P_{SV40E}$, $P_{SV40L}$), the major late promoter of adenovirus ($P_{Adml}$) the promoter of a Vaccinia gene encoding a 7.5 KD protein ($P_{7.5}$), and the promoter of the murine metallothionein gene ($P_{MT}$).

Another vector which may be used for transfection of the desire gene is the retroviral vector pN2-FAT (Garver et al., 1987, supra), which contains the SV40 early promoter directing transcription of the inserted gene in this case, the gene encoding human $\alpha_1$-antitrypsin. The $\alpha_1$-antitrypsin gene can be removed and replaced with a desired gene by digestion with the restriction enzymes HindIII and XhoI (partial), and modification of these ends or the ends of the inserted gene, if necessary, according to conventional techniques.

Retrovirus-mediated gene transfer can be performed by any suitable method, e.g., as described in Wilson et al., 1988, Proc. Nat. Acad. Sci USA 85:3014 for introducing a gene into adult rat hepatocytes, using a replication-defective retrovirus.

TABLE 1

Identification of donor-originating stromal cells in bone marrow explanted from transplanted mice

| | | Donor-originating Glu6PI-a+ cells, % | | |
|---|---|---|---|---|
| Time, mo | GB1/6 cells injected per mouse | Adherent stromal cell explants* per limb, % | | Adherent† stromal cells from right limb LBMCs |
| | | Right | Left | |
| 1 | 0 | <0.01 | <0.01 | Not tested |
| | 1 × 10⁶ | 26.2 ± 3.2 | 28.4 ± 4.4 | Not tested |
| 2 | 0 | <0.01 | <0.01 | <0.01 |
| | 1 × 10⁵ | 75.5 ± 9.5 | 65.0 ± 2 | 76.7 ± 15.7 |
| | 5 × 10⁵ | 82.5 ± 0.5 | 32.5 ± 3.5 | 78.0 ± 0 |
| | 1 × 10⁶ | 59.0 ± 14.4 | 16 ± 0 | Not tested |
| 3 | 0 | <0.01 | <0.01 | <0.01 |
| | 1 ×0 10⁶ | 62.5 ± 12.5 | <0.01 | Not tested |

TABLE 2

Recovery of donor-originating GB1neoʳ cells in cultures explanted from transplanted mice

| | Stromal colonies per hind limb*, no. | | G418-resistant stromal colonies per hind limb†, no. | |
|---|---|---|---|---|
| Group | Right | Left | Right | Left |
| Control- | | | | |
| irradiated | 65.5 ± 4.1 | 110.1 ± 10.3 | 0 | 0 |
| Transplanted | 78.0 ± 13.0 | 98.7 ± 13.3 | 30 ± 2.0 (39 ± 3%) | 10.3 ± 2.0 (11 ± 2%) |

TABLE 3

Hematopoietic recovery in C57BL/6J mice transplanted with GB1/6 stromal cell line

| Total* body dose, Gy | CFU-S per right hind limb,† no. | Peripheral blood analysis on day 42 after irradiation‡ | | |
|---|---|---|---|---|
| | | WBC, × 10³/mm³ | PLT, × 10³/mm³ | RBC, × 10⁶/mm³ |
| 3.0 | 92.0± 24.5 (104.6 ± 26.0) | 8.3 ± 1.5 (7.2 ± 0.3) | 156.5 ± 6.5 (126.5 ± 5.5) | 7.7 ± 0.03 (8.2 ± 0.02) |
| 5.2 | 108.3 ± 9.2 (132.5 ± 24.4) | 6.8 ± 0.3 (5.7 ± 0.6) | 131.5 ± 10.5 (108.0 ± 1.0) | 8.2 ± 0.05 (7.4 ± 0.12) |
| 7.0 | 101.8 ± 11.7§ (49.1 ± 9.5) | 6.9 ± 1.0¶ (4.0 ± 0.05) | 112.5 ± 2.5¶ (50.0 ± 3.0) | 7.5 ± 0.5 (5.9 ± 1.3) |

TABLE 4

| | | Cumulative (7 weeks) | | |
|---|---|---|---|---|
| Stromal Cell Lines | Progenitor Cells | "Cobblestone Island"/Flask | Non-adherent Cells/Flask | Progenitor/ Flask × 10³ |
| Gp-TGFα | 32D-EGFR | 1789.3 ± 106.7 | 6.17 × 10⁶ | 168.8 ± 12.0 |
| | 32DC13 | 0 | 0.06 × 10⁶ | 0 |
| | LTRMCs-d36 | N.T. | 1.67 ×0 10⁶ | 2.0 ± 0.05 |
| GB1/6 | 32D-EGFR | 0 | 1.7 × 10⁶ | 32.5 ± 7.5 |
| | 32DC13 | 0 | 0.007 ×10⁶ | 0 |
| | LTBMCs-d36 | N.T. | 8.1 × 10⁶ | 12.8 ± 0.48 |

We claim:

1. A method of delivering a biologically active, mammalian protein into the bloodstream of a mammal, the method comprising:
    (a) introducing a gene that encodes the protein into isolated bone marrow stromal cells; and
    (b) introducing the bone marrow stromal cells containing the gene into the mammal, wherein the cells produce and secrete the biologically active, mammalian protein into the bloodstream of the mammal.

2. The method of claim 1, wherein the mammal is a human.

3. The method of claim 1, wherein the protein is normally present in the blood.

4. The method of claim 1, wherein the protein is an enzyme.

5. The method of claim 1, wherein the protein is a lymphokine, a growth factor, a hematopoietic factor, or a blood coagulation factor.

6. The method of claim 1, wherein the protein is a growth factor.

7. The method of claim 6, wherein the growth factor is TGF-α.

8. The method of claim 5, wherein the blood coagulation factor is Factor VIII-C.

9. The method of claim 5, wherein the blood coagulation factor is anti-thrombin III.

10. The method of claim 1, wherein the gene introduced into the stromal cells is carried on a retroviral vector.

11. The method of claim 1, wherein the gene introduced into the stromal cells is carried on a eukaryotic vector.

12. The method of claim 1, wherein the gene introduced into the stromal cells is carried on a mammalian expression vector.

13. The method of claim 1, wherein the gene is introduced into the stromal cells by electroporation.

14. The method of claim 1, wherein the gene is introduced into the stromal cells by viral infection.

15. The method of claim 1, wherein the gene is introduced into the stromal cells by retroviral infection.

16. The method of claim 1, wherein the gene is introduced into the stromal cells by viral transfection.

17. The method of claim 1, wherein the gene is introduced into the stromal cells by retroviral transfection.

18. The method of claim 1, wherein the stromal cells are introduced into the same mammal from which they were obtained.

19. The method of claim 1, wherein the stromal cells are introduced into a different mammal than the one from which they were obtained.

20. The method of claim 1, wherein adherence of the stromal cells to a cavity surface of a bone in the mammal is facilitated by irradiation of the bone at a radiation dosage that kills hematopoietic cells, but not stromal cells, in the region of irradiation.

* * * * *